(12) United States Patent
Liu

(10) Patent No.: US 9,161,573 B2
(45) Date of Patent: Oct. 20, 2015

(54) ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 36 days.

(21) Appl. No.: 13/994,710

(22) PCT Filed: Jan. 15, 2013

(86) PCT No.: PCT/CN2013/070488
§ 371 (c)(1),
(2) Date: Jun. 14, 2013

(87) PCT Pub. No.: WO2014/110717
PCT Pub. Date: Jul. 24, 2014

(65) Prior Publication Data
US 2014/0338684 A1    Nov. 20, 2014

(51) Int. Cl.
*A24F 47/00*    (2006.01)
*A61M 15/06*    (2006.01)

(52) U.S. Cl.
CPC .............. *A24F 47/008* (2013.01); *A24F 47/004* (2013.01); *A61M 15/06* (2013.01)

(58) Field of Classification Search
CPC ..... A24F 47/002; A24F 47/008; A24F 47/00; A61M 15/06
USPC ....................... 131/194, 273, 329; 128/202.21
See application file for complete search history.

(56) References Cited

U.S. PATENT DOCUMENTS

2012/0145169 A1*  6/2012  Wu ............................... 131/273

FOREIGN PATENT DOCUMENTS

CN         202206878 U  *  2/2012

OTHER PUBLICATIONS

English Machine Translation of CN202206878U, Sep. 18, 2014.*

* cited by examiner

*Primary Examiner* — Anthony Calandra
(74) *Attorney, Agent, or Firm* — Cheng-Ju Chiang

(57) ABSTRACT

An electronic cigarette includes a liquid storage component and an atomization device. The atomization device includes a hollow spiral tubular electric heater coil and a liquid guiding member passing through the electric heater coil. The liquid guiding member is made from non-glass fiber material. The atomization device further includes a smoke guiding tube passing through the liquid storage component for supporting the same and working as a smoke path. The smoke guiding tube includes an external casing and an internal casing one of which is inserted into another one so as to hold the liquid guiding member between the two. The two ends of the liquid guiding member extend out of the smoke guiding tube and are tightly pressed against an inner wall of the liquid storage component. This kind of electronic cigarette is safe to human body and has stable internal construction.

17 Claims, 5 Drawing Sheets

ELECTRONIC CIGARETTE

FIELD OF THE INVENTION

The present invention relates to field of electronic cigarette and more particularly, relates to an electronic cigarette having an organic cotton liquid guiding member free of glass fiber material.

BACKGROUND OF THE INVENTION

A prior art electronic cigarette includes a liquid storage member for storage of cigar liquid, an atomization device for converting cigar liquid inside the liquid storage member into smoke, and a power supply device for providing power to the atomization device. The atomization device is generally composed of an electronic heater coil, a liquid guiding member, and a smoke guiding tube with a through hole for flowing of smoke. The liquid guiding member and smoke guiding tube are both made of glass fiber containing silicon dioxide. The glass fiber belongs to inorganic materials. The electronic heater coil is enwound on the liquid guiding member, and both ends thereof are connected with electric wire. After that, the electric heater coil is transversely disposed inside the smoke guiding tube. Next, the exposed ends of the electric wire are connected to the positive and negative electrodes of the power supply device. The liquid guiding member is connected to the liquid storage member so as to absorb cigar liquid. Finally, the cigar liquid is transferred to the electric heater coil through the liquid guiding member. When the electric heater coil is powered, smoke will be atomized to generate smoke. As the liquid guiding member and smoke guiding tube of the atomization device are constructed of inorganic materials formed by a great number of tiny glass fibers enwound together, they are susceptible to breaking, bending and twisting. When the electric heater coil is enwound on the liquid guiding member or secured into the smoke guiding tube, the liquid guiding member or smoke guiding tube will be bent or twisted. During this process, a great deal of glass fiber floccules will stick onto the liquid guiding member or inner wall of the smoke guiding tube. When such an electronic cigarette is assembled completely and used, these floccules will easily enter into mouth, respiratory tract or lung of a person, thus resulting in damage to body health. In addition, the smoke guiding tube constructed of glass fiber is easily broken, bent or twisted, thereby having weak structural stability.

SUMMARY OF THE INVENTION

The object of the present invention is to provide an electronic cigarette which is safe to human body and has stable and reliable internal construction.

To realize above object, the present invention provides an electronic cigarette, including a cylindrical liquid storage component for storing cigar liquid, an atomization device for converting cigar liquid contained in the liquid storage component into smoke. The atomization device includes a hollow spiral tubular electric heater coil, a liquid guiding member passing through the electric heater coil so as to support the electric heater coil and absorb and store cigar liquid such that the cigar liquid will be atomized by the electric heater coil. Herein, the liquid guiding member is made from organic cotton materials free of glass fiber. The atomization device further includes a smoke guiding tube passing through the liquid storage component for supporting the same and working as a smoke path. The smoke guiding tube includes an external casing and an internal casing one of which is inserted into another one so as to hold the liquid guiding member between the two and provide working space for the electric heater coil. In addition, the two ends of the liquid guiding member extend out of the smoke guiding tube and are tightly pressed against an inner wall of the liquid storage component.

Here, the atomization device further includes an atomization base disposed in the inner wall of the electronic cigarette for supporting and holding the smoke guiding tube. The internal casing is part of the atomization base, and the atomization base further includes an atomization base body supporting the internal casing.

Here, the internal casing is a tubular component axially outwardly extended from the atomization base body. A first atomization base through hole is defined in the middle portion of the atomization base body and is extended axially therefrom. A second atomization base through hole communicating with the first atomization base through hole is defined in the internal casing and extended axially therefrom. One end of the internal casing far away from the atomization base body is provided with a first holding groove for mounting the liquid guiding member therein.

Here, the first holding groove is an opened groove radially passing through the side wall of the internal casing and having a notch formed in an end portion of the internal casing.

Here, a wire guiding hole axially extended for passing through the electric wire of the electric heater coil is provided on the atomization base body at a location adjacent an outer side of the internal casing.

Here, an expansion ring to be pressed against and engage the inner wall of the electronic cigarette is disposed on the outer wall of the atomization base body.

Here, the smoke guiding tube further includes a supporting tube extended axially outwardly from the external casing and connected to the same. The external casing and supporting tube are integrally formed such that a main guiding tube is formed for flowing of smoke. Both of the supporting tube and external casing are provided with a through hole and the through holes are communicated with each other thus constituting a venting hole of the main guiding tube.

Here, one end of the external casing connected to the atomization base is provided with a second holding groove engaged with the first holding groove of the internal casing.

Here, the second holding groove is an opened groove radially outwardly extended through the side wall of the external casing and having a notch defined in an end portion of the external casing.

Here, the two ends of the liquid guiding member extend out of the external casing, bent, and are pressed against the outer wall of the internal casing so as to be pressed against the liquid storage component.

Here, a permeating component constructed of organic material and with resiliency is disposed between the main guiding tube and liquid storage component.

Here, the permeating component is sleeved on the outer wall of the guiding tube, encircles the liquid guiding member and is tightly pressed against the liquid guiding member.

Here, the permeating component is enwound on the outer wall of the guiding tube, encircles the liquid guiding member, and is tightly pressed against the liquid guiding member.

Here, the liquid guiding member is made of any one or a combination of: pure cotton, paper, chemical fiber containing mainly organic material, or twine.

Here, the permeating component is made of any one or a combination of: pure cotton, paper, chemical fiber containing mainly organic material, or twine.

Using above technical solution, the present invention can gain following advantageous effects. In the present invention, by changing a structure of the atomization device, and making the liquid guiding member, liquid storage component and permeating component with organic cotton materials, there is no need to use inorganic material such as glass fiber, thus reducing cost, improving production efficiency, and most importantly preventing damage caused to human body by inhaling of glass fiber floccules. In addition, by replacement of a smoke guiding tube made of glass fiber with a smoke guiding tube made of plastic, silica gel, metal or ceramic with higher hardness, damage to human body caused by inhaling of glass fiber floccules by the smoker is eliminated effectively. Moreover, the smoke guiding tube is composed of a main guiding tube having the external casing an integral casing. One of the external casing and the internal casing is inserted into the other one so as to mount and secure the liquid guiding member and accordingly, mounting and use of the liquid guiding member is more stable. Due to rapid liquid guiding characteristics of organic cotton material, the temperature of the electric heater coil is decreased, thus ensuring reliability of the electric heater coil in use. In addition, the smoke guiding tube or is made from plastic, silica gel, metal or ceramic and therefore, strength of the smoke guiding tube is guaranteed, and the entire electronic cigarette has a stable internal construction and is safe.

Embodiments of the present invention are further described in conjunction with the accompanying drawings.

DETAILED DESCRIPTION OF THE INVENTION

Figure 1:
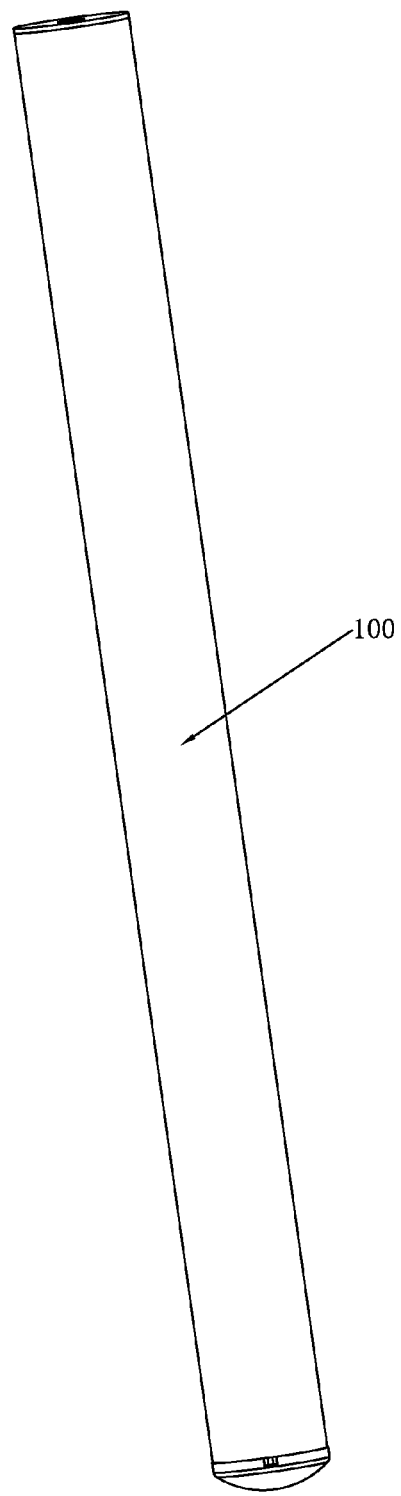
FIG. 1 shows a perspective view of an electronic cigarette of an embodiment of the present invention.

It is noted that, in case no interference is resulted in, the embodiments and features contained therein may be combined with each other. The present invention is described in greater detail in conjunction with the accompanying drawings and embodiments.

As shown in FIGS. 1-7, the present invention provides an electronic cigarette 100. The electronic cigarette 100 is an integral electronic cigarette, and includes a cylindrical outer sleeve 1 in which a liquid storage component 37 for storage of cigar liquid, an atomization device 2 for changing cigar liquid contained in the liquid storage component 37 into smoke, and a power supply device 8 for offering power to the atomization device 2. The two ends of the outer sleeve 1 are provided with a nozzle case 41 and a base cover 42 respectively used as the closure of the outer sleeve 1. Both of the nozzle case 41 and base cover 42 are provided with an intake hole. The electronic cigarette 100 further includes a smoke guiding tube acting as a path for conducting smoke generated by atomization of cigar liquid out of the outer sleeve 1. The smoke guiding tube may be constructed of non-glass fiber material such as silica gel, plastic, ceramic or metal material. In this embodiment, the smoke guiding tube is composed of an internal casing 241 and a main guiding tube 35 which will be described hereinafter.

Figure 2:
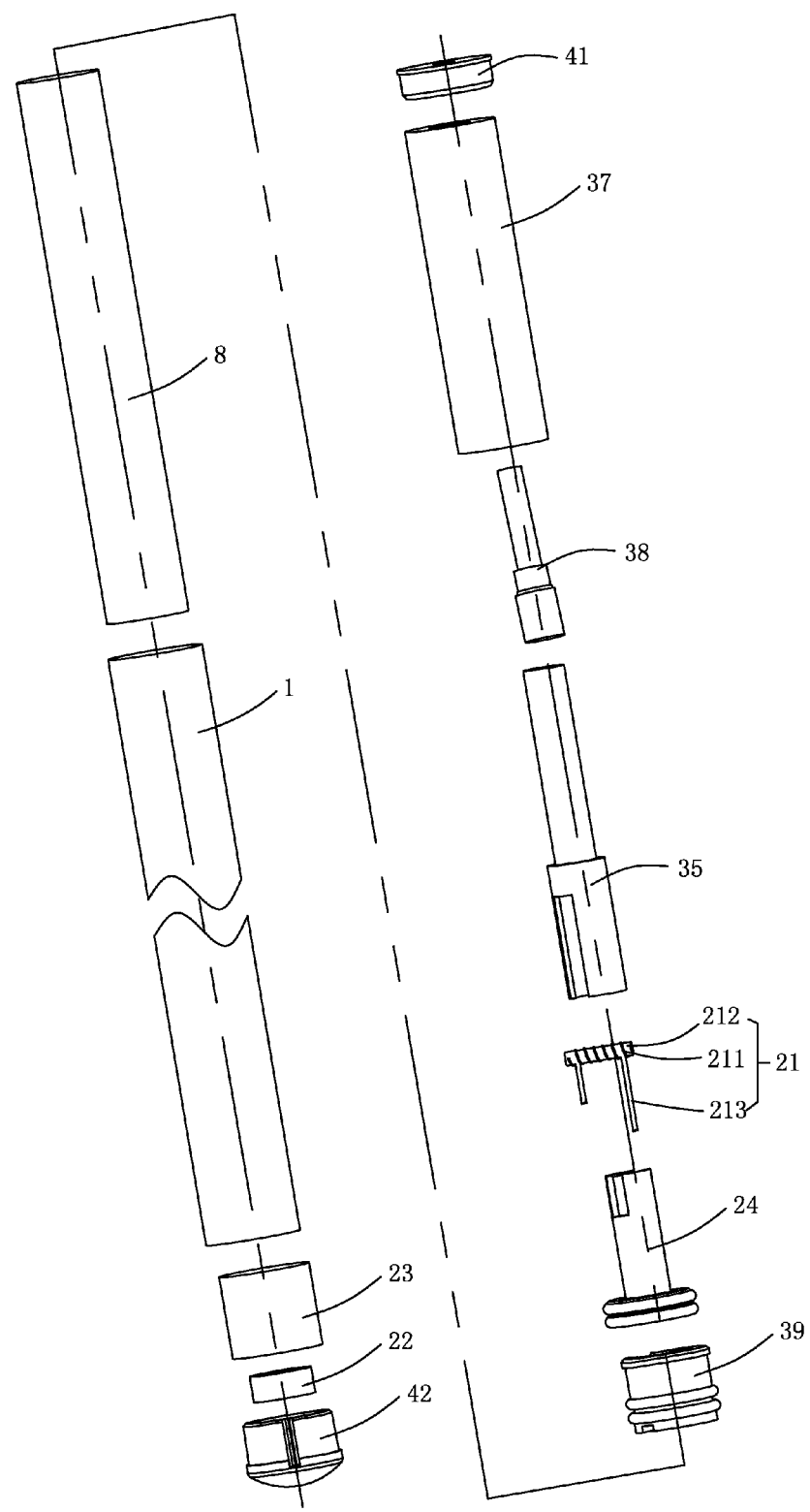
FIG. 2 shows an exploded view of an electronic cigarette of an embodiment of the present invention.
Figure 3:
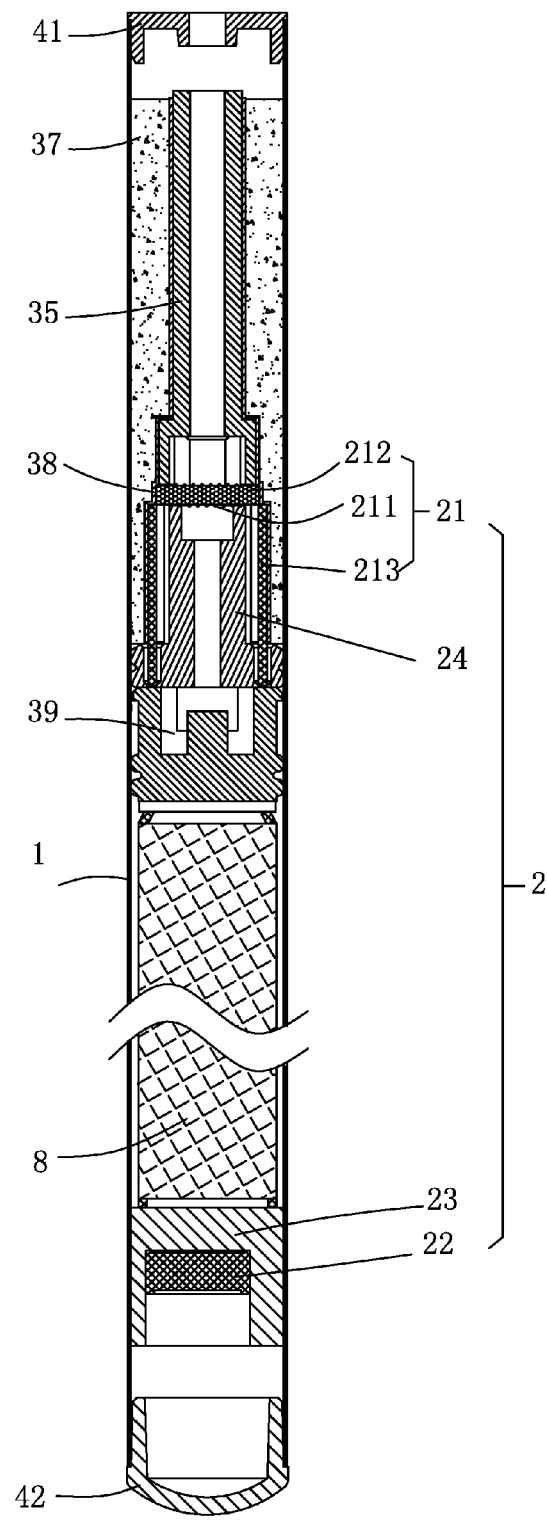
FIG. 3 shows a cross-sectional view of an electronic cigarette of an embodiment of the present invention.

As shown in FIGS. 2 and 3, the atomization device 2 includes an atomizer 21, an atomization base 24 for supporting the atomizer 21, an atomizer control circuit board 22, and a circuit board holding base 23 for receiving and holding the atomizer control circuit board 22. A miniature pneumatic switch is disposed on the atomizer control circuit board 22 for controlling start of the circuit in order that the atomizer 21 will operate. The atomizer 21 is intended for converting cigar liquid into smoke, and includes an electric heater coil 211, a liquid guiding member 212 for absorbing cigar liquid and supporting the electric heater coil 211, and an electric wire 213. The electric heater coil 211 is enwound on the liquid guiding member 212. The liquid guiding member 212 is able to absorb and store cigar liquid. The liquid guiding member 212 is made of non-glass fiber and may be made of material capable of absorbing and storing liquid for example cotton material including pure cotton, paper, chemical fiber or twine. Or, the member 212 may be made of a combination of two or more of above material. In this embodiment, the liquid guiding member 212 is placed and held into the smoke guiding tube. The two ends of the electric heater coil 211 are respectively coupled with a corresponding electric wire 213. The electric wire 213 passes across the atomization base 24 and then is electrically connected with the positive and negative electrodes of the power supply device 8.

Figure 6:
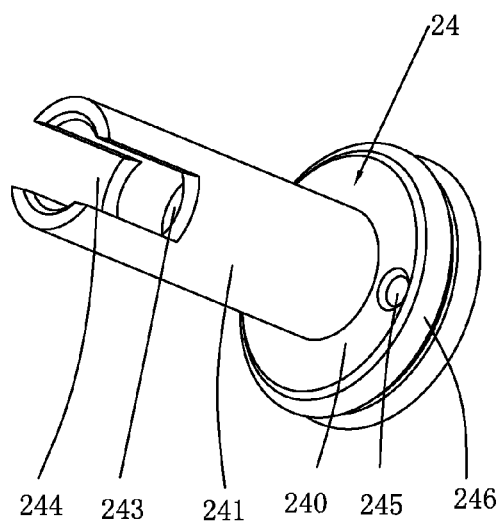
FIG. 6 shows a perspective view of a main guiding tube of an electronic cigarette of an embodiment of the present invention.
Figure 7:
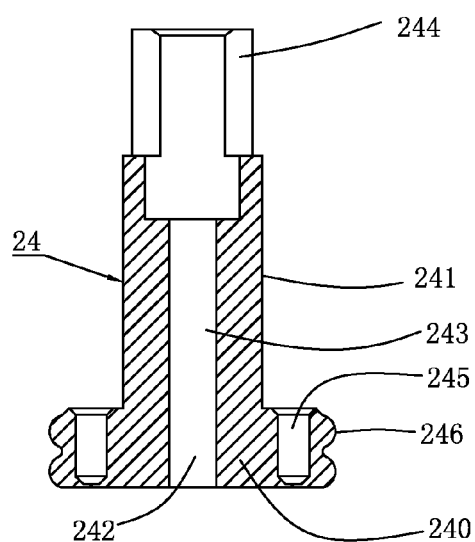
FIG. 7 shows a cross-sectional view of a main guiding tube of an electronic cigarette of an embodiment of the present invention.

As shown in FIGS. 6 and 7, the atomization base 24 includes an atomization base body 240 engaged with the inner wall of the outer sleeve 1, and a tubular internal casing 241 axially outwardly extended from the base body 240. An axially extended first atomization base through hole 242 is defined in the middle portion of the atomization base body 240. An axially extended second atomization base through hole 243 communicating with the first atomization base hole 242 is defined in the internal casing 241. One end of the internal casing 241 far away from the atomization base body 240 is provided with a first holding groove 244. The first holding groove 244 is an opened groove radially passing through the side wall of the internal casing 24 and having a notch formed in an end portion of the internal casing 24 for transversely securing the liquid guiding member 212 and in addition for helping the liquid guiding member 212 be extended out of the internal casing 241 so that the member 212 will contact the liquid storage component 37 for absorbing cigar liquid. Two wire guiding holes 245 axially extended for passing through the electric heater coil 211 are provided on the atomization base body 240 at a location adjacent to an outer side of the internal casing 241. An expansion ring 246 to be pressed against and engage the outer sleeve 1 is disposed on the outer wall of the atomization base body 240. The atomization base 24 is pressed against and held on the inner wall of the outer sleeve 1 by its outer side wall. It is made of plastic or metal for ensuring strength and no glass fiber floccules will be generated.

Figure 4:
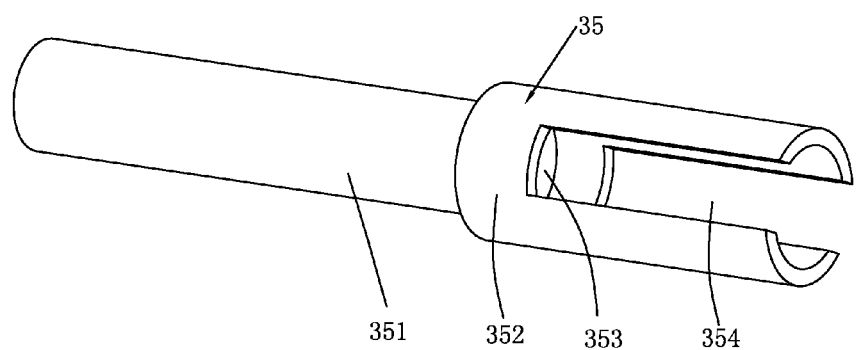
FIG. 4 shows a perspective view of an atomization base of an electronic cigarette of an embodiment of the present invention.
Figure 5:
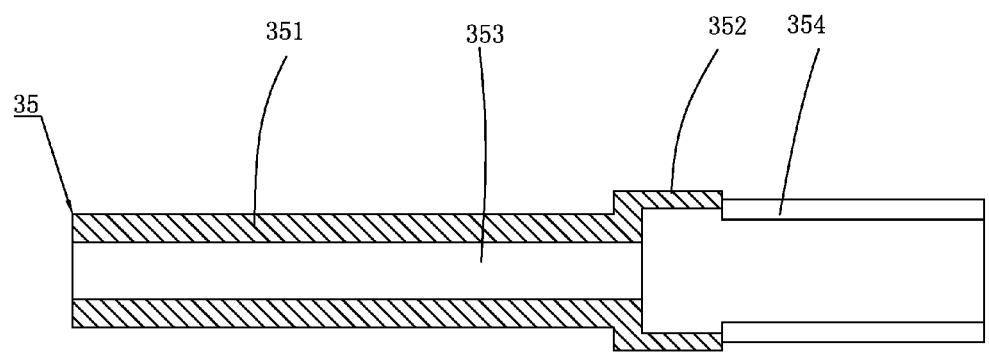
FIG. 5 shows a cross-sectional view of an atomization base of an electronic cigarette of an embodiment of the present invention.

As shown in FIGS. 4 and 5, the main guiding tube 35 includes a supporting tube 351 and an external casing 352 which communicate with each other. The supporting tube 351 and external casing 352 are integrally formed or constructed separately. Both of the supporting tube 351 and external casing 352 are respectively provided with a through hole, and these through holes communicate with each other thus forming a venting hole 353 of the main guiding tube 35. The external casing 352 is provided with a second holding groove 354 engaged with the first holding groove 244 of the internal casing 241. The second holding groove 354 is an opened groove radially outwardly extended through the side wall of the external casing 352 and having a notch defined in an end portion of the external casing 352. The liquid guiding member 212 held in the first holding groove 244 passes through the second holding groove 354 and is pressed against the liquid storage component 37 so as to absorb cigar liquid to be atomized by the electric heater coil 211.

As shown in FIGS. 2 and 3, the liquid storage component 37 is intended for absorbing and storing cigar liquid to be further atomized by the atomizer 2. The liquid storage component 37 has the ability of absorbing and storing cigar liquid, and may be made from material with the ability of absorbing and storing liquid for example cotton material. The liquid storage component 37 is of a hollow cylindrical construction, is sleeved on the outside of the main guiding tube 35, and is pressed against and supported by the outer wall of the main guiding tube 35. The two ends of the liquid storage component 37 are inserted into a circular cavity formed between the atomization base 24 and the outer sleeve 1 and a circular cavity of the nozzle case 41 respectively. The side wall of the liquid storage component 37 is pressed against the liquid guiding member 212. Cigar liquid soaks from the liquid storage component 37 into the liquid guiding member 212, is absorbed, and evaporated by the electric heater coil 211 to generate smoke.

As shown in FIGS. 2 and 3, the electronic cigarette 100 further includes a permeating component 38 capable of absorbing and storing cigar liquid, and may be constructed of non glass fiber material with the ability of absorbing and storing liquid for example organic cotton material. The organic cotton material may be pure cotton, paper with certain hardness, chemical fiber containing mainly organic material, or twine. The permeating component 38 may be made from any one of above material. Or, it may be made from the combination of any two or more of the above material. The permeating component 38 is located between the liquid storage component 37 and the main guiding tube 35. The outer wall and inner wall of the permeating component 38 are pressed against the inner wall of the liquid storage component 37 and outer wall of the external casing 352 of the main guiding tube 35 respectively. The permeating component 38 is sleeved on the outside of the main guiding tube 35 or, it may be enwound on the outer side of the main guiding tube 35 such that the inner wall of the permeating component 38 is pressed against the two ends of the liquid guiding member 212 in order that the liquid guiding member 212 absorbs the cigar liquid soaking from the liquid storage component 37 into the permeating component 38. The liquid absorption ability of the permeating component 38 may be slightly greater than the liquid storage component 37 so that the cigar liquid will be soaked and transported to the liquid guiding member 212 from the liquid storage component 37 more rapidly.

As shown in FIG. 3, in present embodiment, the nozzle case 41, atomization base 24, main guiding tube 35, liquid storage component 37, and part of the side wall of the outer sleeve 1 of the electronic cigarette 100 collectively define a space for storage of cigar liquid which functions as a cigar liquid cup of a traditional electronic cigarette. Here, the atomization base 24 and nozzle case 41 face and are distant from each other and are held on the inner wall of the outer sleeve 1 to define a space range of the cigar liquid cup 3 for storage of cigar liquid. The main guiding tube 35 is axially located between the atomization base 24 and a nozzle case 41. The liquid storage component 37 is radially disposed between the main guiding tube 35 and outer sleeve 1.

As shown in FIGS. 2 and 3, the electronic cigarette 100 further includes a liquid isolating base 39 for preventing leakage of cigar liquid. The liquid isolating base 39 is disposed on the inner wall of the outer sleeve 1, and in addition, it is disposed between the atomization base 24 and power supply device 8 for preventing leakage of cigar liquid from the atomization base 24 into the power supply device 8. A wire guiding hole (not shown) is defined in the bottom wall of the liquid isolating base 39.

In assembling, the liquid guiding member 212 with an electric heater coil 211 installed and enwound thereon is transversely mounted in the first holding groove 244 of the internal casing 241 of the atomization base 24. After that, the internal casing 241 of the atomization base 24 is inserted into the external casing 352 of the main guiding tube 35 ensuring that the liquid guiding member 212 is supported into the first holding groove 244 of the internal casing 241 and two ends thereof extend out of the second holding groove 354 of the main guiding tube 35 and are pressed against the permeating component 38. The two ends of the electric heater coil 211 are connected to the electric wires 213. Each of the electric wires 213 passes through the wire guiding hole 245 of the atomization base 24 and the wire guiding hole of the liquid isolating base 39 and then are connected to the atomizer control circuit board 22. The interface between the electric wires 213 and corresponding guiding holes is sealed.

Though various embodiments of the invention have been illustrated above, a person of ordinary skill in the art will understand that, variations and improvements made upon the illustrative embodiments fall within the scope of the invention, and the scope of the invention is only limited by the accompanying claims and their equivalents.

What is claimed is:

1. An electronic cigarette, comprising a cylindrical liquid storage component for storing cigar liquid, an atomization device for converting cigar liquid contained in the liquid storage component into smoke; wherein the atomization device includes a hollow spiral tubular electric heater coil, a liquid guiding member passing through the electric heater coil so as to support the electric heater coil and absorb and store cigar liquid such that the cigar liquid will be atomized by the electric heater coil; wherein the liquid guiding member is made from non-glass fiber and may be made of material capable of absorbing and storing liquid; the atomization device further comprises a smoke guiding tube passing through the liquid storage component for supporting the same and working as a smoke path; the smoke guiding tube comprises an external casing and an internal casing one of which is inserted into the another one so as to hold the liquid guiding member between the two and provide working space for the electric heater coil; the two ends of the liquid guiding member extend out of the smoke guiding tube and are tightly pressed against an inner wall of the liquid storage component; the atomization device further comprises an atomization base disposed in the inner wall of the electronic cigarette for supporting and holding the smoke guiding tube; the internal casing is part of the atomization base, and the atomization base further comprises an atomization base body supporting the internal casing; the internal casing is a tubular component axially outwardly extended from the atomization base body; a first atomization base through hole is defined in the middle portion of the atomization base body and is extended axially therefrom; a second atomization base through hole communicating with the first atomization base through hole is defined in the internal casing and extended axially therefrom; one end of the internal casing far away from the atomization base body is provided with a first holding groove for mounting the liquid guiding member therein; the smoke guiding tube further comprises a supporting tube extended axially outwardly from the external casing and connected to the same; the external casing and supporting tube are integrally formed such that a main guiding tube is formed for flowing of smoke; both of the supporting tube and external casing are respectively provided with a through hole and the through holes are communicated with each other thus constituting a venting hole of the main guiding tube.

2. The electronic cigarette according to claim 1, wherein the first holding groove is an opened groove radially passing through the side wall of the internal casing and having a notch formed in an end portion of the internal casing.

3. The electronic cigarette according to claim 1, wherein a wire guiding hole axially extended for passing through the electric wire of the electric heater coil is provided on the atomization base body at a location adjacent to an outer side of the internal casing.

4. The electronic cigarette according to claim 1, wherein an expansion ring to be pressed against and engage the inner wall of the electronic cigarette is disposed on the outer wall of the atomization base body.

5. The electronic cigarette according to claim 1, wherein one end of the external casing connected to the atomization base is provided with a second holding groove engaged with the first holding groove of the internal casing.

6. The electronic cigarette according to claim 5, wherein the second holding groove is an opened groove radially outwardly extended through the side wall of the external casing and having a notch defined in an end portion of the external casing.

7. The electronic cigarette according to claim 1, wherein the two ends of the liquid guiding member extend out of the external casing, bent, and are pressed against the outer wall of the internal casing so as to be pressed against the liquid storage component.

8. The electronic cigarette according to claim 7, wherein a permeating component constructed of organic material and with resiliency is disposed between the main guiding tube and liquid storage component.

9. The electronic cigarette according to claim 8, wherein the permeating component is sleeved on the outer wall of the guiding tube, encircles the liquid guiding member and is tightly pressed against the liquid guiding member.

10. The electronic cigarette according to claim 8, wherein the permeating component is enwound on the outer wall of the guiding tube, encircles the liquid guiding member, and is tightly pressed against the liquid guiding member.

11. The electronic cigarette according to claim 8, wherein the permeating component is made of any one or a combination of: pure cotton, paper, chemical fiber containing mainly organic material, or twine.

12. The electronic cigarette according to claim 1, wherein the liquid guiding member is made of any one or a combination of: pure cotton, paper, chemical fiber containing mainly organic material, or twine.

13. An electronic cigarette, comprising a liquid storage component for storing cigar liquid, and an atomization device for converting cigar liquid into smoke; wherein the atomization device includes an electric heater coil, a liquid guiding member passing through the electric heater coil so as to support the electric heater coil and absorb and store cigar liquid such that the cigar liquid will be atomized by the electric heater coil; the atomization device further comprises a smoke guiding tube passing through the liquid storage component for supporting the same and working as a smoke path; the smoke guiding tube comprises an external casing and an internal casing one of which is inserted into the another one so as to hold the liquid guiding member between the two and provide working space for the electric heater coil; the two ends of the liquid guiding member extend out of the smoke guiding tube and contact the liquid storage component against its inner wall for absorbing cigar liquid; the internal casing axially defines a hole therethrough; one end of the internal casing is provided with a first holding groove for mounting the liquid guiding member therein; the smoke guiding tube further comprises a supporting tube extended axially outwardly from the external casing and connected to the same; the external casing and supporting tube are integrally formed such that a main guiding tube is formed for flowing of smoke; both of the supporting tube and external casing are provided with a through hole and the through holes are communicated with each other thus constituting a venting hole of the main guiding tube and further communicated with the hole of the internal casing.

14. An electronic cigarette, comprising a liquid storage component for storing cigar liquid, and an atomization device for converting cigar liquid into smoke; wherein the atomization device includes an atomizer and a smoke guiding tube passing through the liquid storage component for supporting the same and forming a smoke path therethrough; the smoke guiding tube comprises an external casing and an internal casing one of which is inserted into the another one so as to hold the atomizer between the two and provide working space for the atomizer; the internal casing axially defines a through hole therein; one end of the internal casing is provided with a first holding groove for mounting the atomizer therein; a supporting tube axially extending from the external casing and connected to the same; the external casing and the supporting tube integrally form a main guiding tube for flowing of smoke therethrough; a venting hole is defined in the main guiding tube and further communicated with the through hole of the internal casing to form the smoke path.

15. The electronic cigarette according to claim 14, wherein one end of the external casing connected to the internal casing is provided with a second holding groove engaged with the first holding groove of the internal casing whereby to hold the atomizer and provide working space for the atomizer; the first and second holding grooves are opened grooves radially outwardly extended through an side wall of the internal casing or the external casing, and each holding groove has a notch defined in an end portion of the internal casing or the external casing.

16. The electronic cigarette according to claim 15, wherein the atomizer comprises a hollow spiral tubular electric heater coil, a liquid guiding member passing through the electric heater coil so as to support the electric heater coil and absorb and store cigar liquid such that the cigar liquid will be atomized by the electric heater coil; and the liquid guiding member is made from material capable of absorbing and storing liquid and free of glass fiber; the liquid guiding member is held in the first holding groove, passes through the second holding groove, and is pressed against the liquid storage component so as to absorb cigar liquid to be atomized by the electric heater coil.

17. The electronic cigarette according to claim 16, wherein the liquid guiding member is made of from any one or combination of: pure cotton, paper, chemical fiber containing mainly organic material, or twine.

* * * * *